United States Patent [19]

Chauvin et al.

[11] Patent Number: 5,550,306
[45] Date of Patent: Aug. 27, 1996

[54] CATALYTIC PROCESS FOR THE DIMERIZATION OF OLEFINS

[75] Inventors: Yves Chauvin, Rueil Malmaison, France; Sandra Einloft, Rio Grande Do Sul, Brazil; Helene Olivier, Rueil Malmaison, France

[73] Assignee: Institut Francais du Petrole, Rueil Malmaison, France

[21] Appl. No.: 456,820

[22] Filed: Jun. 1, 1995

Related U.S. Application Data

[62] Division of Ser. No. 309,702, Sep. 21, 1994.

[30] Foreign Application Priority Data

Sep. 22, 1993 [FR] France .................................. 93 11381

[51] Int. Cl.⁶ ............................................. C07C 2/24
[52] U.S. Cl. ...................... 585/514; 585/510; 585/520; 585/527
[58] Field of Search ................................. 585/510, 514, 585/520, 527

[56] References Cited

U.S. PATENT DOCUMENTS

| | | | |
|---|---|---|---|
| 4,087,379 | 5/1978 | de Hault et al. | 252/459 B |
| 5,104,840 | 4/1992 | Chauvin et al. | 502/117 |

FOREIGN PATENT DOCUMENTS

| | | |
|---|---|---|
| 0448445 | 9/1991 | European Pat. Off. . |
| 2220493 | 10/1974 | France . |

*Primary Examiner*—Ponnathapura Achutamurthy
*Attorney, Agent, or Firm*—Millen, White, Zelano, & Branigan, P.C.

[57] ABSTRACT

The invention is concerned with a process for the dimerization, co-dimerization and oligomerization of olefins with a catalytic composition resulting from mixing at least one quaternary ammonium halide and/or at least one quaternary phosphonium halide, at least one aluminum halide, at least one aromatic hydrocarbon and optionally an aluminium organometallic compound.

22 Claims, No Drawings

CATALYTIC PROCESS FOR THE DIMERIZATION OF OLEFINS

This is a division, of the application Ser. No. 08/309,702 filed Sep. 21, 1994, now pending.

BACKGROUND OF THE INVENTION

The present invention is concerned with a catalytic composition and a process which uses that composition for the dimerization, codimerization and oligomerization of olefins, and, in particular, propylene, the composition resulting from dissolving a nickel compound mixed or complexed with a phosphine in the liquid mixture of ionic type of quaternary ammonium halide and/or quaternary phosphonium halide, aluminium halide, an aromatic hydrocarbon and optionally an aluminium alkyl compound.

French Patent 2611700 describes the use of liquids of the ionic type formed from quaternary aluminium halides and ammonium halides as solvents of organometallic nickel complexes for dimerization catalysis of olefins. The use of such media which are immiscible with aliphatic hydrocarbons, particularly with end products of olefin dimerization makes better use of homogeneous catalysts possible. U.S. Pat. No. 5,104,840 describes a liquid composition of the ionic type resulting from contacting quaternary ammonium halides and/or quaternary phosphonium halides with aluminium alkyl dihalides and possibly also an aluminium trihalide. This same patent describes the use of these media as solvents of transition metal complexes, particularly nickel complexes not containing a nickel-carbon bond which are transformed into olefin oligomerisation catalysts. Hereinafter, these media will be called "molten salts" because they are in a liquid state at a moderate temperature.

During the work undertaken, it has been seen that the most active and most stable nickel catalysts are obtained in "molten salts" constituted by a molar equivalent of ammonium halide and/or phosphonium halide with one equivalent and more of aluminium trihalide, and optionally any quantity of aluminium alkyl dihalide. This formulation was seen to be particularly worthwhile because the nickel complexes dissolved there had a high degree of catalytic activity which was constant with the passage of time.

However, it has been seen that under such conditions "the phosphine effect" described by G. Wilke et al in Ind. Eng Chem., 1970, 62, No. 12, P34 and in GB Patent 1.058.680 which manifests itself by the influence which the substituents provided by the phosphorus atom have on the way in which the propylene molecules are interlinked during catalytic dimerization by nickel, rapidly disappears with the passage of time. This unexplained phenomenon has unfortunate consequences since it is not possible to obtain the desired selectivities.

SUMMARY OF THE INVENTION

It has now been discovered that by adding an aromatic hydrocarbon to a "molten salt" it is possible to overcome this problem and catalysts result of high and stable activity and with a high degree of selectivity in terms of the most branched isomers.

Thus, the invention relates to a catalytic composition comprising at least one nickel compound mixed or complexed with at least one tertiary phosphine, dissolved at least partly in a non-aqueous medium of ionic type resulting from the contacting of at least one aluminium halide (B) with at least one quaternary ammonium halide and/of at least one quaternary phosphonium halide (A), and with at least one aromatic hydrocarbon (C).

To be more exact the object of the invention is a process for the dimerization, codimerization or oligomerisation of at least one olefin, in which process the olefin is contacted with at least one nickel compound mixed or complexed with at least one tertiary phosphine, said compound being dissolved at least partly in a non-aqueous medium of ionic type, the process being characterised in that said medium results from contacting at least one aluminium halide with at least one quaternary ammonium halide and/or quaternary phosphonium halide and with at least one aromatic hydrocarbon.

The medium of the "molten salt" type is thus constituted by:
a) halides, most particularly quaternary ammonium and/or quaternary phosphonium chlorides and/or bromides (called product A);
b) aluminium halide and preferably chloride, bromide (called product B);
c) simple, condensed or substituted aromatic hydrocarbon (called product C);
d) optionally an aluminium organic derivative (called product D).

The quaternary ammonium halides and quaternary phosphonium halides which can be used within the scope of the invention preferably correspond to the general formulae $NR^1R^2R^3R^4X$ and $PR^1R^2R^3R^4X$ where X represents Cl or Br, $R^1$, $R^2$, $R^3$ and $R^4$ which may be the same or different, each representing hydrogen, an alkyl, aliphatic (saturated or unsaturated) or aromatic group comprising 1 to 12 carbon atoms. The quaternary ammonium halides and/or phosphonium halides can also be heterocycle derivatives comprising 1, 2 or 3 nitrogen and/or phosphorus atoms. By way of example, tetrabutylphosphonium chloride, N-butylpyridinium chloride, ethyl pyridinium bromide, 3-butyl 1-methyl imidazolium chloride, diethylpyrazolium chloride, pyridinium hydrochloride, trimethylphenyl ammonium chloride may be cited.

The aromatic hydrocarbons according to the invention are benzene and its substitutes of the general formula $C_6H_xR_{6-x}$, R being an alkyl, cycloalkyl, aryl, alkylaryl radical such as $C_6H_5CH_2$, and x taking the values of 1 to 5; naphthalene and its substitutes of the general formula $C_{10}H_xR_{8-x}$, R being defined as hereinabove and x being between 0 and 7; anthracene and its derivatives of the general formula $C_{14}H_xR_{12-x}$ where R is as defined hereinabove and x is equal to 0 to 9 inclusive.

They can be used alone or mixed. By way of example, benzene, toluene, xylenes, durene and isodurene, pentamethylbenzene, hexamethylbenzene, a-methylnaphthalene, 2,6-dimethylanthracene can be cited.

The organic derivatives of aluminium according to the invention are of the general formula $AlR_xX_{3-x}$ in which R is an alkyl, linear or branched radical comprising 2 to 8 carbon atoms, X being chlorine or bromine and x having a value of 1, 2 or 3. By way of example, dichloroethylaluminium, ethylaluminium sesquichloride, isobutylaluminium sesquichloride, dichloroisobutylaluminium and chlorodiethylaluminium can be used.

The "molten salt" components, as defined hereinabove, are used in A: B molar ratios of between 1:0.5 and 1:3, preferably of between 1:1 and 1:2; B:C of between 1:1 and 1:100, preferably of between 1:1 and 1:10 and B:D of between 1:0 and 1:10, preferably of between 1:0.01 and 1:5. It is nevertheless necessary for the components and the proportions of them to be such that the mixture is liquid at the temperature at which the nickel compound and phosphine are introduced, although the catalytic dimerization reaction can take place at a temperature above or below the melting temperature of the catalytic compound. If the aromatic hydrocarbon is divided between the polar phase and the hydrocarbon phase constituted by the dimers and the oligomers, it is necessary to add some of the aromatic hydrocarbon continuously so that its concentration in the polar phase remains within the bracket given above.

The compounds which enter into the composition according to the invention can be mixed in any order. The mixture can be formed by simple contacting followed by agitation until a homogeneous liquid is formed. The mixture can be made outside the dimerization reactor, or preferably in the reactor.

The nickel compounds according to the invention are chloride, bromide, sulphate, carboxylates, e.g. 2-ethyl hexanoate, phenates, acetyl acetonate, mixed with a tertiary phosphine, or their complexes with a tertiary phosphine. It is also possible to use organometallic complexes of nickel which may, or may not, contain phosphines.

The phosphines according to the invention correspond to the general formulae $PR^1R^2R^3$ and $R^1R^2P—R'—PR^1R^2$ in which $R^1$, $R^2$ and $R^3$ which may be the same or different are alkyl, cycloalkyl, aryl or aralkyl radicals comprising 1 to 10 carbon atoms, and R' is an aliphatic bivalent residue with 1 to 6 carbon atoms.

By way of example, it is possible to cite:

triisopropylphosphine, tricyclohexylphosphine, tribenzylphosphine, dicyclohexylphenylphosphine, tetra cyclohexylmethylene-diphosphine diisopropyltertiobutylphosphine.

Examples of nickel compounds which can be used according to the invention are $NiCl_2,2P(isopropyl)_3$, $NiCl_2, 2P(cyclohexyl)_3$, $NiCl_2,2pyridine$ complexes mixed with a triisopropylphosphine equivalent, nickel chloride mixed with a triisopropylphosphine equivalent, nickel acetate mixed with a tricyclohexylphosphine equivalent, pallylnickeltriisopropylphosphine chloride.

The olefins which can be dimerized or oligomerised by the catalytic compositions according to the invention are ethylene, propylene, n-butenes, and n-pentenes, on their own or in a mixture, pure or diluted with an alkane such as found in "cuts" from petroleum refining processes, such as catalytic cracking or steam cracking processes.

The catalytic reaction of the dimerization of olefins can be carried out in a closed system, in a semi-open system or continuously in one or more reaction stages. Vigorous agitation will ensure good contact between the reagent(s) and the catalytic composition. The reaction temperature can be between $-40°$ and $+70°$ C., preferably between $-20°$ and $+50°$ C. It is possible to operate above or below the melting temperature of the catalytic composition, the dispersed solid state not restricting good progress of the reaction. The heat generated by the reaction can be eliminated using any means known to the skilled person. The pressure can be between 0.1 MPa and 20 MPa, preferably between atmospheric pressure and 5 MPa. The reaction products and the reagent(s) which have not reacted are separated from the catalytic system by simple decantation, and then fractioned.

The following examples will illustrate the invention, without limiting the scope thereof.

EXAMPLE 1

Preparation of the ionic solvent 17.5 g (0.1 mole) of imidazolium butylmethyl chloride, 16.3 g (0.122 mole) of sublimed aluminium chloride, 0.26 g (0.002 mole) of dichloroethylaluminium and 4.02 g (0.03 mole) of isodurene are mixed at ambient temperature. A clear yellow liquid is thus obtained.

Dimerization of the propylene

A 100 ml glass reactor provided with a temperature measuring probe, a bar magnet to ensure good agitation and a double lining to enable cooling liquid to circulate was purged of air and humidity, and kept at atmospheric pressure with propylene of 99% purity. 45 mg (0.1 mmole) of $NiCl_2,2P(iPr)_3$ complex was introduced, and the temperature was then lowered to $-15°$ C. and a syringe was used to inject 3.5 ml of the liquid composition prepared above and 7 ml heptane. Agitation was begun and absorption of the propylene was immediately observed. When the reactor was three-quarters full of liquid, agitation was stopped, the "molten salt" was allowed to decant, and most of the hydrocarbon phase was drawn off. The operation was started again seven times, after which time a total of 430 g of propylene had been introduced. An analysis which was made of the various fractions showed that they were composed of 85% dimers, 12% trimers and 3% tetramers. The composition of dimers which was practically identical in all the fractions comprised 81% 2,3-dimethyl butenes, 2% n-hexenes and 17% 2-methylpentenes. This content of dimethylbutenes was far greater to that described by G. Wilke.

EXAMPLE 1' (COMPARATIVE)

Preparation of an ionic solvent

An ionic solvent was prepared under the same conditions as those of the previous example, except that no aromatic hydrocarbon was added. The liquid was practically colourless under these conditions.

Dimerization of the propylene

The same procedure was followed as in the previous example. The first hydrocarbon fraction was seen to be composed of 83% dimers, 14% trimers and 3% tetramers; the dimers contained 83% 2,3-dimethylbutenes, 2% n-hexanes and 15% 2-methyl pentenes. The dimers of the seventh fraction which still represented 85% of the products did not contain more than 11% 2,3-dimethyl butenes alongside 16% n-hexanes and 63% 2-methyl pentenes. The composition of the last fraction was particularly low in dimethylbutenes.

EXAMPLE 2

Dimerization of propylene

The same procedure was followed as in Example 1, except that instead of 45 mg $NiCl_2,2P(iPr)_3$ 69 mg (0.1 mmole) of $NiCl_2,2P(cyclohexyl)_3$ complex was introduced. Three drawing off operations were carried out which corresponded to 210 g of the propylene introduced. The three fractions were made up of 78% dimers, 18% trimers and 4% tetramers. The dimers contained 84% 2,3-dimethylbutenes, 1% n-hexanes and 15% 2-methylpentenes. The dimers were particularly rich in dimethylbutenes.

EXAMPLE 3

Preparation of the ionic solvent

The same procedure was followed as in Example 1, except that the isodurene was replaced with 4.26 g a-methylnaphthalene.

Dimerization of propylene

The same procedure was followed as in Example 1, except that the "molten salt" used was that prepared for the purpose, and 50 mg (0.12 mmole) of $NiCl_2,2PiPr_3$ complex was introduced. Three drawing off operations were carried out. The first fraction was composed of 78% dimers containing 84% 2,3-dimethylbutenes. The last fraction was composed of 88% dimers containing 65% 2,3-dimethylbutenes.

EXAMPLE 4

Preparation of the ionic solvent

The same procedure was followed as in Example 1, except that the isodurene was replaced with 4.4 g of pentamethylbenzene.

Dimerization of propylene

The same procedure was followed as in Example 1, except that the "molten salt" used was that prepared for the purpose, and that 50 mg (012 mmole) of $NiCl_2,2PiPr_3$ was introduced. Six drawing off operations were carried out, corresponding to 370 g of the propylene introduced. The first fraction was composed of 79% dimers containing 83% 2,3-dimethylbutenes. The last fraction was composed of 84% dimers containing 75% 2,3-dimethyl butenes.

EXAMPLE 5

This example illustrates the case where the aromatic hydrocarbon, toluene in this example, is divided between the polar phase and the phase constituted by the oligomers. It is thus added after each drawing off operation.

Preparation of the ionic solvent

The same procedure was followed as in Example 1, except that the isodurene was replaced by 2.46 g toluene.

Dimerization of the propylene

The same procedure was followed as in Example 1, except that the "molten salt" used was that prepared for the purpose, and 50 mg (0.12 mmole) of the $NiCl_2,2PiPr_3$ complex was introduced. Six drawing off operations were carried out, corresponding to 370 g of the propylene introduced. After each drawing off operation, 0.2 mL toluene was added. The first fraction was composed of 78% dimers containing 83% 2,3-dimethylbutenes. The last fraction was composed of 78% dimers containing 83% 2,3-dimethylbutnes. In an identical test where no toluene was added after each drawing off operation the last fraction did not contain more than 10% dimethylbutenes.

Naturally, in a continuous process, the toluene would be added continuously or periodically to the mixture agitated with the catalytic composition and reaction products.

We claim:

1. A process for the dimerization, codimerization or oligomerization of at least one olefin, comprising contacting the olefin with at least one nickel compound mixed or complexed with at least one tertiary phosphine, said compound being dissolved at least partly in a non-aqueous ionic medium, said medium resulting from contacting: (C) at least one aromatic hydrocarbon with (B) at least one aluminum halide and with (A) at least one quaternary ammonium halide and/or at least one quaternary phosphonium halide, said aromatic hydrocarbon being selected from the group consisting of unsubstituted benzene, substituted benzene of the formula $C_6H_xR_{6-x}$ wherein x is equal to 1 to 5 inclusive; unsubstituted naphthalene, substituted naphthalene of the formula $C_{10}H_xR_{8-x}$ and x is equal to 0 to 7 inclusive, unsubstitued anthracene, and substituted anthracene of the formula $C_{14}H_xR_{10-x}$ and x is equal to 0 to 9 inclusive, wherein R is an alkyl, cycloalkyl, aryl, alkaryl radical, the A:B molar ratio being between 1:0.5 and 1:3, and the B:C molar ratio being between 1:1 and 1:100.

2. A process according to claim 1 in which the reaction temperature is between −40° C. and +70° C. and the pressure is between 0.1 and 20 MPa.

3. A process according to claim 1 in which the reaction temperature with the olefin is between −20° C. and +50° C.

4. A process according to claim 1 in which aromatic hydrocarbon is introduced during the reaction with the olefin.

5. A process according to claim 2 in which the reaction temperature with the olefin is between −20° C. and +50° C.

6. A process according to claim 2 in which aromatic hydrocarbon is introduced during the reaction with the olefin.

7. A process according to claim 3 in which aromatic hydrocarbon is introduced during the reaction with the olefin.

8. A process according to claim 5 in which aromatic hydrocarbon is introduced during the reaction with the olefin.

9. A process according to claim 1, wherein the said quaternary ammonium halide is selected from the group consisting of n-butyl pyridinium chloride, ethylpyridinium bromide, 3-butyl chloride 1-methyl imidazolium, diethyl pyrazolium chloride and N-butylpyridinium chloride.

10. A process according to claim 1, wherein the said quaternary phosphonium halide is tetrabutylphosphonium chloride.

11. A process according to claim 1, wherein the said aluminum halide is aluminum chloride.

12. A process according to claim 1, wherein the aromatic hydrocarbon is toluene, axylene, durene, isodurene, pentamethylbenzene, a-methylnaphthalene, or 2,6-dimethylanthracene.

13. A process according to claim 1, wherein the nickel compound is a chloride, bromide, sulphate, actylacetonate, carboxylate, or phenate.

14. A process according to claim 1, wherein the non-aqueous medium also contains an organic aluminum derivative (D) of the general formula: $AlR_xX_{3-x}$ wherein R is a linear or branched alkyl radical comprising 2 to 8 carbon atoms, X is chlorine or bromine and x is equal to 1, 2, or 3.

15. A process according to claim 14, wherein the organic aluminum derivative is selected from the group consisting of dichloroethylaluminum, dichloroisobutylaluminum, chlorodiethylaluminum, ethylaluminum sesquichloride, and diisobutylaluminum sesquichloride.

16. A process according to claim 14, wherein the B:D molar ratio is between 1:0 and 1:10.

17. A process according to claim 1, said process being run continuously wherein the aromatic hydrocarbon is divided between a polar phase and a hydrocarbon phase comprising dimers and oligomers, and wherein the aromatic hydrocarbon concentration in the polar phase is maintained by periodic or continuous additions thereto.

18. A process according to claim 1, wherein said process, over time, results in a higher percentage of dimethyl substituted olefins than in a comparable process conducted without the aromatic hydrocarbon.

19. A process according to claim 18, wherein the olefin oligomerized is propylene and the resultant dimethyl substituted olefin is 2,3-dimethylbutene.

20. A process according to claim 14, wherein said process, over time, results in a higher percentage of dimethyl substituted olefins than in a comparable process conducted without the aromatic hydrocarbon.

21. A process according to claim 20, wherein the olefin oligomerized is propylene and the resultant dimethyl substituted olefin is 2,3-dimethylbutene.

22. A process for the oligomerization of propylene to selectively produce 2,3-dimethylbutene, said process comprising contacting propylene with at least one nickel compound mixed or complexed with at least one tertiary phosphine, said compound being dissolved at least partly in a non-aqueous ionic medium, said medium resulting from contacting (C) at least one aromatic hydrocarbon with (B) aluminum chloride, with (A) a quaternary ammonium halide selected from the group consisting of n-butyl pyridinium chloride, ethylpyridinium bromide, 3-butyl chloride 1-methyl imidazolium, diethyl pyrazolium chloride and n-butylpyridinium chloride; and (D) an organic aluminum derivative selected from the group consisting of dichloroethylaluminum, dichloroisobutylaluminum, chlorodiethylaluminum, ethylaluminum sesquichloride, and diisobutylaluminum sesquichloride;

said aromatic hydrocarbon being toluene, xylenes, durene, isodurene, pentamethylbenzene, amethylnaphthalene, or 2,6-dimethylanthracene;

said nickel compound being a chloride, bromide, sulphate, acetylacetonate, carboxylate, or phenate;

the A:B molar ratio being between 1:0.5 and 1:3, the B:C ratio being between 1:1 and 1:100, and the B:D molar ratio being between 1:0 and 1:10.

* * * * *